US011166964B2

(12) United States Patent
Halpern et al.

(10) Patent No.: US 11,166,964 B2
(45) Date of Patent: Nov. 9, 2021

(54) TREATMENT FOR MODULATING GUT MICROBIOTA

(71) Applicant: Galmed Research and Development Ltd., Tel Aviv (IL)

(72) Inventors: Maya Halpern, Kfar Tavor (IL); Allen Baharaff, Tel Aviv (IL)

(73) Assignee: Galmed Research and Development Ltd, Tel Aviv (IL)

( * ) Notice: Subject to any disclaimer, the term of this patent is extended or adjusted under 35 U.S.C. 154(b) by 681 days.

(21) Appl. No.: 16/070,626

(22) PCT Filed: Jan. 19, 2017

(86) PCT No.: PCT/IL2017/050075
§ 371 (c)(1),
(2) Date: Jul. 17, 2018

(87) PCT Pub. No.: WO2017/125929
PCT Pub. Date: Jul. 27, 2017

(65) Prior Publication Data
US 2021/0169901 A1 Jun. 10, 2021

(30) Foreign Application Priority Data

Jan. 20, 2016 (IL) .......................... 243707

(51) Int. Cl.
| *A61K 31/575* | (2006.01) |
| *A61K 47/54* | (2017.01) |
| *A61P 1/04* | (2006.01) |
| *A61K 9/00* | (2006.01) |
| *A61K 35/747* | (2015.01) |
| *A61K 45/06* | (2006.01) |
| *A61K 47/36* | (2006.01) |
| *A61K 47/38* | (2006.01) |

(52) U.S. Cl.
CPC .......... *A61K 31/575* (2013.01); *A61K 9/0031* (2013.01); *A61K 9/0053* (2013.01); *A61K 35/747* (2013.01); *A61K 45/06* (2013.01); *A61K 47/36* (2013.01); *A61K 47/38* (2013.01); *A61K 47/542* (2017.08); *A61P 1/04* (2018.01)

(58) Field of Classification Search
CPC .................................................. A61K 31/575
See application file for complete search history.

(56) References Cited

U.S. PATENT DOCUMENTS

| 5,783,215 A | 7/1998 | Arwidsson et al. |
| 5,866,619 A | 2/1999 | Sintov et al. |
| 6,384,024 B1 | 5/2002 | Gilat |
| 6,395,722 B1 | 5/2002 | Gilat |
| 6,562,829 B1 | 5/2003 | Pines et al. |
| 6,565,883 B2 | 5/2003 | Ogorka et al. |
| 6,589,946 B2 | 7/2003 | Gilat |
| 7,501,403 B2 | 3/2009 | Gilat |
| 8,110,564 B2 | 2/2012 | Gilat |
| 8,729,046 B2 | 5/2014 | Rogler et al. |
| 8,858,954 B2 | 10/2014 | Hsu et al. |
| 8,975,246 B2 | 3/2015 | Gilat |
| 9,498,484 B2 | 11/2016 | Fiorucci et al. |
| 9,763,964 B2 | 9/2017 | Pellicciari et al. |
| 2011/0014126 A1 | 1/2011 | Evans et al. |
| 2014/0187633 A1 | 7/2014 | Manku et al. |
| 2016/0023983 A1 | 1/2016 | Gagnon et al. |
| 2016/0213702 A1 | 7/2016 | Von Maltzahn |
| 2019/0175619 A1 | 6/2019 | Hayardeny-Nissimov et al. |

FOREIGN PATENT DOCUMENTS

| EP | 2632925 | 4/2013 |
| JP | 2009-514788 | 9/2009 |
| JP | 2010-506958 | 4/2010 |
| WO | WO 1999/052932 | 10/1999 |
| WO | WO 2002/083147 | 10/2002 |
| WO | WO 2010/086864 | 8/2010 |
| WO | WO 2014/093711 | 6/2014 |
| WO | WO 2014/121298 A2 | 8/2014 |
| WO | WO 2014/121302 A2 | 8/2014 |
| WO | WO 2014/197738 | 12/2014 |
| WO | WO 2015/019358 A1 | 2/2015 |
| WO | WO 2015/019359 A1 | 2/2015 |
| WO | WO 2015/083164 A1 | 6/2015 |
| WO | WO 2015/124637 A1 | 8/2015 |
| WO | WO 2015/186126 | 12/2015 |
| WO | WO 2016/094570 | 6/2016 |
| WO | WO 2016/112305 | 7/2016 |
| WO | WO 2016/154258 | 9/2016 |

(Continued)

OTHER PUBLICATIONS

Anumah, I. et al. (2017). Liver Fibrosis: Mechanisms of Development, Experimental Models and Treatment Strategies. Research Journal of Pharmaceutical Biological and Chemical Sciences, 8(2), 682-695.
Aramchol Demonstrates Significant Anti-fibrotic effect in a pre-clinical model of fatty liver disease, on line, Mar. 30, 2016, URL: http://galmedpharma.investorroom.com/2016-03-30-Aramchol-Demonstrates-Significant-Anti-Fibrotic-in-a-Pre-clinical-Model-of-Fatty-Liver-Disease.
Bansal, R. et al. (2016). Clinical advancements in the targeted therapies against liver fibrosis. Mediators of inflammation, 2016.
Brodosi, L. et al. (2017). NASH: A glance at the landscape of pharmacological treatment. Annals of hepatology, 15(5), 673-681.
Cao et al. "Secondary bile acid-induced dysbiosis promotes intestinal carcinogenesis" International journal of cancer. Jun. 1, 2017;140(11):2545-56.

(Continued)

*Primary Examiner* — Rosanne Kosson
(74) *Attorney, Agent, or Firm* — Mark S. Cohen; Pearl Cohen Zedek Latzer Baratz LLP

(57) ABSTRACT

The present invention is directed to the modulation of gut microbiota. Specifically, the invention relates to pharmaceutical compositions for use in restoring gastrointestinal homeostasis and in alleviating gastrointestinal disorders and other conditions associated with imbalance of gut flora. More specifically, the invention relates to the use of compositions comprising a therapeutically effective amount of a fatty acid bile acid conjugate (FABAC).

23 Claims, No Drawings

(56) References Cited

FOREIGN PATENT DOCUMENTS

| WO | WO 2017/017677 | 2/2017 |
|---|---|---|
| WO | WO 2017/210526 | 12/2017 |

OTHER PUBLICATIONS

De Oliveira da Silva, B. et al. (2017). Molecular interplays in hepatic stellate cells: apoptosis, senescence, and phenotype reversion as cellular connections that modulate liver fibrosis. Cell biology international, 41(9), 946-959.

Erejuwa et al. "Modulation of gut microbiota in the management of metabolic disorders: the prospects and challenges. International journal of molecular sciences" Mar. 2014;15(3):4158-88.

Gilat et al. "Dissolution of cholesterol gallstones in mice by the oral administration of a fatty acid bile acid conjugate" Hepatology. Mar. 2002;35(3):597-600.

Iruarrizaga-Lejarreta, M. et al. (2017). Role of Aramchol in steatohepatitis and fibrosis in mice. Hepatology communications, 1(9), 911-927.

Kurikawa, N. et al. (2013). A novel inhibitor of stearoyl-CoA desaturase-1 attenuates hepatic lipid accumulation, liver injury and inflammation in model of nonalcoholic steatohepatitis. Biological and Pharmaceutical Bulletin, 36(2), 259-267.

Leikin-Frenkel, A. et al. (2008). Treatment of preestablished diet-induced fatty liver by oral fatty acid-bile acid conjugates in rodents. European journal of gastroenterology & hepatology, 20(12), 1205-1213.

Leikin-Frenkel, A. et al. (2010). Fatty acid bile acid conjugate inhibits hepatic stearoyl coenzyme A desaturase and is non-atherogenic. Archives of medical research, 41(6), 397-404.

Neuschwander-Tetri, B. A. et al. & NASH Clinical Research Network. (2015). Farnesoid X nuclear receptor ligand obeticholic acid for non-cirrhotic, non-alcoholic steatohepatitis (FLINT): a multicentre, randomised, placebo-controlled trial. The Lancet, 385(9972), 956-965.

Noureddin, M. et al. (2016). Emerging anti-fibrotic therapies in the treatment of non-alcoholic steatohepatitis. Alimentary pharmacology & therapeutics, 43(11), 1109-1123.

Noureddin, M. et al. (2016). Promising therapies for treatment of nonalcoholic steatohepatitis. Expert opinion on emerging drugs, 21(3), 343-357.

Powell, D. A. (2014). An overview of patented small molecule stearoyl coenzyme-A desaturase inhibitors (2009-2013). Expert opinion on therapeutic patents, 24(2), 155-175.

Ratziu, V. et al. (2016). Elafibranor, an agonist of the peroxisome proliferator-activated receptor-α and -δ, induces resolution of non-alcoholic steatohepatitis without fibrosis worsening. Gastroenterology, 150(5), 1147-1159.

Safadi et al. "The fatty acid-bile acid conjugate aramchol reduces liver fat content in patients with nonalcoholic fatty liver disease" Clinical Gastroenterology and Hepatology. Dec. 1, 2014;12(12):2085-91.

Sanyal, A. J. et al. (2010). Pioglitazone, vitamin E, or placebo for nonalcoholic steatohepatitis. New England Journal of Medicine, 362(18), 1675-1685.

T Pritchard, M. et al. (2015). Identifying novel targets for treatment of liver fibrosis: what can we learn from injured tissues which heal without a scar?. Current drug targets, 16(12), 1332-1346.

Trovato, F. M. et al. (2014). 4Ps medicine of the fatty liver: the research model of predictive, preventive, personalized and participatory medicine—recommendations for facing obesity, fatty liver and fibrosis epidemics. EPMA Journal, 5(1), 1-24.

Trauner et al. "Bile acids as modulators of gut microbiota linking dietary habits and inflammatory bowel disease: a potentially dangerous liaison" Gastroenterology. Apr. 1, 2013;144(4):844-6.

VAJro et al. "Microbiota and gut-liver axis: a mini-review on their influences on obesity and obesity related liver disease" Journal of pediatric gastroenterology and nutrition. May 2013;56(5):461.

A Clinical Trial to Evaluate the Efficacy and Safety of two Aramchol Doses versus Placebo in Patients with NASH (Aramchol_005), on line, Oct. 31, 2014, URL: https://clinicaltrials.gov/ct2/show/NCT02279524.

Search Report issued for Corresponding PCT Application No. PCT/IB2017/001521.

Search Report issued for Corresponding PCT Application No. PCT/IL2014/051052.

Search Report issued for Related PCT Application No. PCT/IL2016/050595.

Supplementary European Search Report dated Jul. 29, 2019 for EP Application No. 17741187.

International Search Report dated Mar. 21, 2017 for PCT Application No. PCT/IL2017/050075.

TREATMENT FOR MODULATING GUT MICROBIOTA

CROSS-REFERENCE TO RELATED APPLICATIONS

This application is a § 371 national stage of PCT International Application No. PCT/IL2017/050075, filed Jan. 19, 2017, claiming priority of Israeli Patent Application No. 243707, filed Jan. 20, 2016, the contents of each of which are hereby incorporated by reference into the application.

FIELD OF THE INVENTION

The present invention is directed to the modulation of gut microbiota, specifically to medicaments useful in restoring gastrointestinal homeostasis and in alleviating gastrointestinal disorders.

BACKGROUND OF THE INVENTION

The human gastrointestinal (GI) tract, the largest microbial reservoir in the body, harbors about $10^{14}$ microorganisms, predominantly bacteria. These microorganisms are collectively referred to as microbiota, while their collective genomes constitute what is known as the microbiome. The normal microbiota typically consist of 500-1000 different species, primarily inhabiting the colon, of which Firmicutes and Bacteroidetes species represent more than 90%. GI bacterial populations vary in their qualitative composition and abundance from the proximal to the distal portion, and from inner to outer lumen, and are influenced by the subject's age, dietary habits, geographical origin, type of birth, antibiotic therapies, and exposure to environmental stimuli (Vajro et al., 2013, *J Pediatr Gastroenterol Nutr*, May; 56(5):461-8).

The gut microbiota is involved in a number of physiological functions including digestion, metabolism, extraction of nutrients, synthesis of vitamins, prevention of pathogen colonization, and immune modulation. Alterations or changes in composition and biodiversity of the gut microbiota have been observed in various metabolic states and in many gastrointestinal disorders and other pathophysiological conditions. For example, microbiota disruptions or alterations have been associated or correlated with cases of obesity, inflammatory bowel disease (IBD), celiac disease, irritable bowel syndrome (IBS), colon cancer, diabetes, liver disorders, cystic fibrosis and allergies. Thus, specific microbiota profiles have been evaluated as markers for various pathophysiological states. At present, the interplay between the development of such pathologies and changes in microbiota composition and diversity is yet to be fully elucidated. Thus, studies aimed at investigating this interplay, attempting to determine whether a particular microbial alteration results from the development of a pathology of interest, and whether (and to what extent) it contributes to its etiology, are emerging as an intriguing field of study (Vajro et al., 2013, ibid; Erejuwa et al., 2014, *Int J Mol Sci*, March 7; 15(3): 4158-88).

Various approaches of modulating the gut microbiota have been reported. Such approaches include for example probiotics (administration of live microorganisms), prebiotics (digestion resistant dietary supplements that selectively enhance the growth and/or activity of a particular resident gut microbe), antimicrobial agents (e.g. antibiotics), as well as more indirect approaches such as surgery and weight loss strategies. In view of evidence that links the disruption in the composition and diversity of the gut microbiota to the development of certain pathologies, approaches aimed at modulating the gut microbiota have been suggested as potential therapies. However, while some studies reported on favorable results, others have failed to report any therapeutic benefit, or even described aggravation or deterioration of the condition or its symptoms (Erejuwa et al., 2014, ibid). Thus, research investigating the role of gut microbiota in disease development, and in particular the prospects of microbial modulation as a therapeutic approach, is still in its infancy, and necessitates more rigorous in vitro, animal, and clinical studies.

Fatty acid bile salt conjugates, referred to also as Fatty Acid Bile Acid Conjugates (FABACs), are a family of synthetic molecules that may be used to improve conditions related to bile acids or cholesterol metabolism. FABACs are believed to lower blood cholesterol concentration, reduce liver fat levels and dissolve gallstones (Gilat et al., *Hepatology* 2003; 38: 436-442; and Gilat et al., *Hepatology* 2002; 35: 597-600). FABAC include inter alia 3β-arachidylamido-7α,12α-dihydroxy-5β-cholan-24-oic acid, also known as Aramchol.

U.S. Pat. Nos. 6,384,024, 6,395,722, 6,589,946 disclose certain FABACs and their use in dissolving cholesterol gallstones in bile and treating arteriosclerosis. These and additional FABACs were disclosed in U.S. Pat. Nos. 7,501, 403, 8,975,246 and 8,110,564 for use in treating fatty liver, in reducing blood cholesterol levels and in treating hyperglycemia, diabetes, insulin resistance and obesity. Further therapeutic uses of FABACs are disclosed in Safadi et al. (*Clin Gastroenterol Hepatol*. 2014 December; 12(12):2085-91) and in WO 2015/019358 and WO 2015/019359. Amine salts of certain FABACs are disclosed in WO 2015/083164.

WO 2014/121298 and WO 2014/121302 refer to the use of purified populations of spore-forming bacteria, and to therapeutic compositions containing non-pathogenic, germination-competent bacterial spores. These publications suggest the use of various culture media supplements including Oxgall (dehydrated bovine bile, composed of fatty acids, bile acids, inorganic salts, sulfates, bile pigments, cholesterol, mucin, lecithin, glycuronic acids, porphyrins, and urea) for in vitro purposes, namely in germinating populations of bacterial spores in vitro.

US 2016/0213702 relates to preparations of glycan therapeutics, pharmaceutical compositions and medical foods thereof, optionally comprising micronutrients, polyphenols, prebiotics, probiotics or other agents, and methods of making same. Also provided are methods of using the glycan therapeutics, e.g. for the modulation of human gastrointestinal microbiota and to treat dysbioses. US 2016/0213702 further discloses that said glycan therapeutics may be used for the treatment of metabolic disorders such as NAFLD and NASH. Aramchol is mentioned merely among hitherto known treatments for NAFLD/NASH. Glycan therapeutics are disclosed as comprising branched glycans that comprise glucose, galactose, arabinose, mannose, fructose, xylose, fucose, or rhamnose glycan units, further defined by particular parameters including their average degree of branching and polymerization.

WO 2015/124637 relates to a preparation from animal, artificial, synthetic, cultured and/or fermented stool, made by suspending the stool in a liquid and by depletion of the microbiota comprised in the suspension analogue to or by filtrating the suspension with a filter having a maximum pore size of <450 nm, for use as a medicine.

There exists an unmet medical need for effective treatments specifically aimed at improving or restoring gut microbiota. In addition, there remains a need for additional and improved therapies for alleviating gastrointestinal disorders, or other conditions involving gut flora imbalance as part of their etiology.

SUMMARY OF THE INVENTION

The present invention is directed to the modulation of gut microbiota. Specifically, the invention relates to pharmaceutical compositions for use in modifying gastrointestinal (GI) microbial populations and in alleviating GI disorders and other conditions associated with imbalance of gut flora. More specifically, the invention relates to the use of compositions comprising a therapeutically effective amount of a fatty acid bile acid conjugate (FABAC). According to certain advantageous embodiments, the FABAC is 3β-arachidylamido-7α, 12α-dihydroxy-5β-cholan-24-oic acid (Aramchol) or a pharmaceutically acceptable salt thereof.

According to a first aspect of the present invention, there is provided a pharmaceutical composition for use in treating or preventing dysbiosis in a subject in need thereof, the composition comprising a therapeutically effective amount of a FABAC of Formula I:

W—X-G　　　　　　　　　　　　　　　　　　　(I)

wherein G represents a bile acid or a bile salt radical thereof; W represents one or two fatty acid radicals having 6-22 carbon atoms; and X represents a bonding member selected from the group consisting of: a heteroatom, a direct C—C bond and a C=C bond.

According to some embodiments, the bonding member is selected from the group consisting of: NH, P, S, O and a direct C—C or C=C bond. Each possibility represents a separate embodiment of the present invention. According to some embodiments, the bonding member is NH.

The term "dysbiosis" as used herein refers to a state of the microbiota of the gut or other body area in a subject, in which the normal diversity and/or function of the microbial populations is disrupted. This unhealthy state can be due to a decrease in diversity, the overgrowth of one or more pathogens or pathobionts, symbiotic organisms able to cause disease only when certain genetic and/or environmental conditions are present in a subject, or the shift to an ecological microbial network that no longer provides an essential function to the host subject, and therefore no longer promotes health. According to non-limitative examples, essential functions may include enhancement of the gut mucosal barrier, direct or indirect reduction and elimination of invading pathogens, enhancement of the absorption of specific substances, and suppression of GI inflammation.

In one embodiment, the dysbiosis is dysbiosis of the GI tract. In various embodiments, the composition may be used for improving (modulating or shifting towards a desired composition and distribution of) GI microbiota populations. In another embodiment, the composition is for use in promoting the growth of beneficial microbiota in the GI tract. In another embodiment the composition is for use in inhibiting the growth of detrimental microbiota in the GI tract. In another embodiment, the composition is for use in modifying (e.g. enhancing) microbiota biodiversity in the GI tract.

According to some embodiments, each of said one or two fatty acid radicals is a radical of a fatty acid selected from the group consisting of: arachidic acid, stearic acid, behenic acid, palmitic acid, arachidonic acid, eicosapentaenoic acid and oleic acid. Each possibility represents a separate embodiment of the present invention. According to some embodiments, said one or two fatty acid radicals are radicals of arachidic acid. Each possibility represents a separate embodiment of the present invention.

According to some embodiments, W represents two fatty acid radicals, each independently comprises 6-22 carbon atoms; and each of said fatty acid radicals is independently bound to a bonding member X selected from the group consisting of: a heteroatom, a direct C—C bond and a C=C bond. According to some embodiments, W represents a single fatty acid radical. Each possibility represents a separate embodiment of the invention.

According to some embodiments, the bile acid is selected from the group consisting of: cholic acid, ursodeoxycholic acid, chenodeoxycholic acid, deoxycholic acid, lithocholic acid and derivatives thereof. Each possibility represents a separate embodiment of the present invention. According to some embodiments, the bile acid is cholic acid.

In another embodiment, the bonding member is selected from the group consisting of: NH, P, S, O and a direct C—C or C=C bond; each of said one or two fatty acid radicals is a radical of a fatty acid selected from the group consisting of: arachidic acid, stearic acid, behenic acid, palmitic acid, arachidonic acid, eicosapentaenoic acid and oleic acid; and the bile acid is selected from the group consisting of: cholic acid, ursodeoxycholic acid, chenodeoxycholic acid, deoxycholic acid, lithocholic acid and derivatives thereof.

In a particular embodiment, said FABAC is 3β-arachidylamido-7α, 12α-dihydroxy-5β-cholan-24-oic acid (Aramchol) or a pharmaceutically acceptable salt thereof. In another embodiment Aramchol is in the form of Aramchol free acid. In another embodiment Aramchol is in the form of an amine-based salt. In certain particular embodiments, the salt is a meglumine, lysine or tromethamine Aramchol salt. Each possibility represents a separate embodiment of the invention.

In another embodiment the compositions of the invention comprise said conjugate as the active ingredient and further comprise at least one of a pharmaceutically acceptable excipient, diluent or carrier. In another embodiment said composition is formulated for oral administration. According to certain other embodiments, said composition is formulated as a controlled release formulation, enabling (enhanced or targeted) delivery of the active ingredient to particular regions of the GI tract (e.g. to the jejunum, duodenum, ileum and/or the colon). In another embodiment, said composition is for localized jejunal, duodenal, ileal or colonic delivery, e.g. by infusion. In another embodiment said composition is formulated for rectal administration. Each possibility represents a separate embodiment of the invention.

In another embodiment, the compositions of the invention comprise the FABAC (e.g. Aramchol) as a sole active ingredient. Yet in other embodiments, the composition may contain additional active ingredients. In various embodiments, said composition further comprises (or is for use in combination with) at least one antibiotic, probiotic or prebiotic agent. For example, the composition may further comprise or be administered in combination with antibiotic agents (including, but not limited to nitroimidazoles, macrolides, or beta-lactams), probiotic agents (including, but not limited to *lactobacillus* species such as *Lactobacillus casei, Lactobacillus plantarum, Lactobacillus acidophilus*, and *Lactobacillus rhamnosus*), and/or prebiotic agents (including, but not limited to dietary fibers or agents such as or lactulose, lignin, cellulose, hemicelluloses, β-glucans, pectin, gums, resistant starch, dextrin, *psyllium*, inulin, fructooligosaccharides, and polydextrose). In another embodiment, said composition comprises or is used in combination with a fecal microbiota transplant (FMT). In another embodiment said composition is used in combination with a prescribed diet, including, but not limited to a fiber-enriched, fructose-reduced, elemental, total liquid enteral, total parenteral, or peripheral parenteral diet. Each possibility represents a separate embodiment of the invention.

According to various embodiments, the dysbiosis may be associated with a gastrointestinal disease or disorder. For example, said dysbiosis may be associated with a chronic inflammatory disease, an autoimmune disease, an infection, bowel resection, and/or a condition associated with chronic diarrhea. According to exemplary embodiments, the disease or disorder may be selected from the group consisting of irritable bowel syndrome (IBS), inflammatory bowel disease (IBD, including Crohn's Disease and colitis), short bowel syndrome (SBS), celiac disease, small intestinal bacterial overgrowth (SIBO), gastroenteritis, leaky gut syndrome, and gastric lymphoma. In another embodiment, the disease or disorder is associated with a bacterial, viral or parasitic infection or overgrowth. In a particular embodiment, the disease or disorder is associated with infection by drug-resistant bacteria. Each possibility represents a separate embodiment of the invention.

In another embodiment, the subject is human According to embodiments of the invention, the compositions of the invention may be used for treating a subject exhibiting dysbiosis (for example one or more symptoms thereof as disclosed herein). According to yet other embodiments, the compositions of the invention may be used prophylactically, for protecting and maintaining normal GI flora. Thus, in another embodiment, the composition is for use in preventing dysbiosis in a subject at risk of developing dysbiosis (for example due to exposure to antibiotics or other factors which may disrupt the normal GI flora, including, but not limited to immune compromised subjects and patients in intensive care settings, or patients following surgical manipulations of the GI tract). According to particular embodiments, said subject is under a treatment regimen with at least one agent selected from the group consisting of anti microbial agents, parenteral nutrition, or immune suppressive agents. Each possibility represents a separate embodiment of the invention.

In another aspect, there is provided a pharmaceutical composition for use in preventing and/or treating a gastrointestinal pathology associated with alternation of intestinal flora balance in a subject in need thereof, the composition comprising a therapeutically effective amount of a FABAC of Formula I as defined herein.

In a particular embodiment, said FABAC is Aramchol or a pharmaceutically acceptable salt thereof. In another embodiment Aramchol is in the form of Aramchol free acid. In another embodiment Aramchol is in the form of an amine-based salt. In certain particular embodiments, the salt is a meglumine, lysine or tromethamine Aramchol salt. Each possibility represents a separate embodiment of the invention.

In various embodiments, said dysbiosis is associated with a chronic inflammatory disease, an autoimmune disease, an infection, bowel resection, and/or a condition associated with chronic diarrhea. According to particular embodiments, the pathology is selected from the group consisting of: irritable bowel syndrome (IBS), inflammatory bowel disease (IBD), short bowel syndrome (SBS), celiac disease, small intestinal bacterial overgrowth (SIBO), gastroenteritis, leaky gut syndrome, and gastric lymphoma. In another embodiment the disease or disorder is associated with a bacterial, viral or parasitic infection or overgrowth, e.g. by drug-resistant bacteria. According to other embodiments, the composition is formulated as described herein, or used in combination with additional agents as described herein. Each possibility represents a separate embodiment of the invention.

In a particular embodiment, said FABAC is Aramchol or a pharmaceutically acceptable salt thereof. In another embodiment Aramchol is in the form of Aramchol free acid. In another embodiment Aramchol is in the form of an amine-based salt. In certain particular embodiments, the salt is selected from the group consisting of meglumine, lysine and tromethamine Aramchol salts. Each possibility represents a separate embodiment of the invention.

In another aspect there is provided a method for treating or preventing dysbiosis in a subject in need thereof, comprising administering to the subject a pharmaceutical composition comprising a therapeutically effective amount of a FABAC of Formula I as defined herein.

In one embodiment, the bonding member is selected from the group consisting of: NH, P, S, O and a direct C—C or C=C bond; each of said one or two fatty acid radicals is a radical of a fatty acid selected from the group consisting of: arachidic acid, stearic acid, behenic acid, palmitic acid, arachidonic acid, eicosapentaenoic acid and oleic acid; and the bile acid is selected from the group consisting of: cholic acid, ursodeoxycholic acid, chenodeoxycholic acid, deoxycholic acid, lithocholic acid and derivatives thereof. In another embodiment the FABAC is 3β-arachidylamido-7α,12α-dihydroxy-5β-cholan-24-oic acid (Aramchol), or a pharmaceutically acceptable salt thereof.

In another embodiment the dysbiosis is dysbiosis of the GI tract. According to some embodiments, the method is used for promoting the growth of beneficial microbiota in the GI tract, inhibiting the growth of detrimental microbiota in the GI tract and/or modifying microbiota biodiversity in the GI tract. In another embodiment the dysbiosis is associated with a gastrointestinal disease or disorder. In another embodiment said dysbiosis is associated with a chronic inflammatory disease, an autoimmune disease, an infection, bowel resection, and/or a condition associated with chronic diarrhea. In another embodiment the disease or disorder is selected from the group consisting of: IBS, IBD, SBS, celiac disease, SIBO, gastroenteritis, leaky gut syndrome, and gastric lymphoma. In another embodiment the disease or disorder is associated with a bacterial, viral or parasitic infection or overgrowth. In another embodiment the disease or disorder is associated with infection by drug-resistant bacteria.

In another embodiment the subject is human. In some embodiments said subject exhibits dysbiosis, or is at risk for developing dysbiosis. In another embodiment said subject is under a treatment regimen with at least one of anti microbial agents, parenteral nutrition, or immune suppressive agents.

In another embodiment said composition comprises the FABAC as a sole active ingredient. In another embodiment said composition comprises the FABAC in combination with at least one antibiotic, probiotic or prebiotic agent. In another embodiment said composition comprises the FABAC in combination with a FMT. In another embodiment said composition is formulated for oral administration. In some embodiments said composition is formulated as a controlled release formulation enabling jejunal, duodenal, ileal or colonic delivery of said FABAC, or is administered by localized jejunal, duodenal, ileal or colonic delivery by infusion. In another embodiment said composition is formulated for rectal administration. In another embodiment the method comprises administering said FABAC in combination with a diet selected from the group consisting of: fiber-enriched, fructose-reduced, elemental, total liquid enteral, total parenteral, and peripheral parenteral diet.

In another aspect there is provided a method for preventing and/or treating a gastrointestinal pathology associated with alternation of intestinal flora balance in a subject in need thereof, comprising administering to the subject a pharmaceutical composition comprising a therapeutically effective amount of a FABAC of Formula I as defined herein. In another embodiment said FABAC is Aramchol or a pharmaceutically acceptable salt thereof.

In another embodiment said dysbiosis is associated with a chronic inflammatory disease, an autoimmune disease, an infection, bowel resection, and/or a condition associated with chronic diarrhea. In another embodiment the disease or disorder is selected from the group consisting of: IBS, IBD, SBS, celiac disease, SIBO, gastroenteritis, leaky gut syndrome, and gastric lymphoma. In another embodiment the disease or disorder is associated with a bacterial, viral or parasitic infection or overgrowth. In a particular embodiment the disease or disorder is associated with infection by drug-resistant bacteria.

In another embodiment said composition comprises the FABAC as a sole active ingredient. In another embodiment said composition comprises the FABAC in combination with at least one antibiotic, probiotic or prebiotic agent. In a particular embodiment said composition comprises the FABAC in combination with a FMT.

In various embodiments said composition is formulated for oral administration or for rectal administration. In certain other embodiments, said composition is formulated as a controlled release formulation enabling jejunal, duodenal, ileal or colonic delivery of said FABAC, or is administered by localized jejunal, duodenal, ileal or colonic delivery by infusion. In another embodiment the method comprises administering said FABAC in combination with a diet selected from the group consisting of: fiber-enriched, fructose-reduced, elemental, total liquid enteral, total parenteral, and peripheral parenteral diet.

In another aspect, there is provided a pharmaceutical composition comprising a therapeutically effective amount of a FABAC of Formula I as defined herein, e.g. Aramchol or a pharmaceutically acceptable salt thereof, in combination with at least one antibiotic, probiotic or prebiotic agent. In certain embodiments, the antibiotic agent may include, but is not limited to, nitroimidazoles (e.g. metronidazole), macrolides (e.g. Erythromycin, Azithromycin), and beta-lactams (e.g. Ampicillin or derivatives thereof). In some embodiments, the probiotic agent comprises e.g. at least one of *Lactobacillus casei, Lactobacillus plantarum, Lactobacillus acidophilus*, and *Lactobacillus rhamnosus*. In another embodiment, the probiotic agent may be a fecal microbiota transplant (FMT). Each possibility represents a separate embodiment of the invention.

In various other exemplary embodiments, said composition is formulated as a controlled release formulation enabling (enhanced or targeted) jejunal, duodenal, ileal or colonic delivery of said FABAC. In other embodiments said composition is formulated for oral or rectal administration. According to further embodiments, said composition is formulated for localized jejunal, duodenal, ileal or colonic delivery by infusion.

In another embodiment, said composition is used for the preparation of a medicament for preventing and/or treating dysbiosis or a gastrointestinal pathology associated therewith in a subject in need thereof, including, but not limited to IBS, IBD, SBS, celiac disease, SIBO, gastroenteritis, leaky gut syndrome, and gastric lymphoma, or a pathology associated with a bacterial, viral or parasitic infection or overgrowth. Each possibility represents a separate embodiment of the invention.

In another aspect there is provided a kit comprising Aramchol or a pharmaceutically acceptable salt thereof and instructions for use thereof in combination with at least one antibiotic, probiotic or prebiotic agent, for the treatment or prevention of dysbiosis or a gastrointestinal pathology associated therewith. According to particular embodiments, the antibiotic agent may be selected from the group consisting of nitroimidazoles, macrolides, and beta-lactams; the prebiotic agent may be selected from the group consisting of lactulose, lignin, cellulose, hemicelluloses, β-glucans, pectin, gums, resistant starch, dextrin, *psyllium*, inulin, fructooligosaccharides, and polydextrose; and the probiotic agent may comprise at least one *lactobacillus* species or a FMT. In another embodiment, the kit further comprises said at least one antibiotic, probiotic or prebiotic agent. According to other particular embodiments, the pathology may be e.g. IBS, IBD, SBS, celiac disease, SIBO, gastroenteritis, leaky gut syndrome, and gastric lymphoma, or a pathology associated with a bacterial, viral or parasitic infection or overgrowth. Each possibility represents a separate embodiment of the invention.

Other objects, features and advantages of the present invention will become clear from the following description and drawings.

DETAILED DESCRIPTION OF THE INVENTION

The present invention is directed to the modulation of gut microbiota. Specifically, the invention relates to compositions and methods for restoring gastrointestinal homeostasis, for modifying gastrointestinal microbiota profiles at various levels of the GI tract, and for alleviating gastrointestinal disorders and other conditions associated with imbalance of gut flora. More specifically, the invention relates to the use of compositions comprising a therapeutically effective amount of a fatty acid bile acid conjugate (FABAC), such as 3β-arachidylamido-7α, 12α-dihydroxy-5β-cholan-24-oic acid (Aramchol) or a pharmaceutically acceptable salt thereof.

In one aspect there is provided a pharmaceutical composition for use in treating or preventing dysbiosis in a subject in need thereof, the composition comprising a therapeutically effective amount of a FABAC of Formula I:

$$W-X-G \qquad (I)$$

wherein G represents a bile acid or a bile salt radical thereof; W represents one or two fatty acid radicals having 6-22 carbon atoms; and X represents a bonding member selected from the group consisting of: a heteroatom, a direct C—C bond and a C=C bond. In a particular embodiment said FABAC is Aramchol or a pharmaceutically acceptable salt thereof.

In another aspect there is provided a method for treating or preventing dysbiosis in a subject in need thereof, comprising administering to the subject a pharmaceutical composition comprising a therapeutically effective amount of a FABAC of Formula I as defined herein, e.g. Aramchol or a pharmaceutically acceptable salt thereof.

In another aspect there is provided a pharmaceutical composition for use in preventing and/or treating a gastrointestinal pathology associated with alternation of intestinal flora balance in a subject in need thereof, the composition comprising a therapeutically effective amount of a FABAC of Formula I as defined herein, e.g. Aramchol or a pharmaceutically acceptable salt thereof.

In another aspect there is provided a method for preventing and/or treating a gastrointestinal pathology associated with alternation of intestinal flora balance in a subject in need thereof, comprising administering to the subject a pharmaceutical composition comprising a therapeutically effective amount of a FABAC of Formula I as defined herein, e.g. Aramchol or a pharmaceutically acceptable salt thereof.

In another aspect, the invention relates to a pharmaceutical composition comprising a therapeutically effective amount of a FABAC of Formula I as defined herein, e.g. Aramchol or a pharmaceutically acceptable salt thereof, in combination with at least one antibiotic, probiotic or prebiotic agent.

In another aspect the invention relates to a kit comprising a FABAC of Formula I as defined herein (such as Aramchol or a pharmaceutically acceptable salt thereof) and instructions for use thereof in combination with at least one antibiotic, probiotic or prebiotic agent, for the treatment or prevention of dysbiosis or a gastrointestinal pathology associated therewith.

In another embodiment, there is provided a pharmaceutical composition for use in modifying the microbiome profile in a subject in need thereof, the composition comprising a therapeutically effective amount of a FABAC of Formula I as defined herein, e.g. Aramchol or a pharmaceutically acceptable salt thereof.

Fatty Acid Bile Acid Conjugates

As used herein, the terms "FABAC", "FABACs", "BAFACs", "the FABACs" and "the FABACs of the invention" are used interchangeably and refer to conjugates of the Formula W—X-G (Formula I), wherein G represents a bile acid or a bile salt radical thereof, W represents one or two fatty acid radical(s) having 6-22 carbon atoms, and X represents a bonding member between said bile acid and the fatty acid radical(s). According to some embodiments, bonding member X includes, but is not limited to, NH, P, S, O or a direct C═C or C—C bond. Each possibility represents a separate embodiment of the present invention. FABACs are known in the art, and are described, for example, in U.S. Pat. Nos. 6,384,024, 6,395,722, and 6,589,946, the contents of which are incorporated herein by reference. According to some embodiments, the one or two fatty acid radical(s) comprise 8-22 carbon atoms, possibly 14-22 carbon atoms, preferably 18-22 carbon atoms. Each possibility represents a separate embodiment of the present invention. Typically and preferably, the bond is a solid bond that is not substantially deconjugated by intestinal and/or bacterial enzymes. An ester bond is thus not suitable according to these embodiments since it is easily deconjugated. The bond stands in particular for NH but may also stand for other suitable bonding members, e.g. S, P, O-ether, etc. The bond can be in the alpha or beta configuration and can be attached in various positions of the bile acid molecule, positions 3, 6, 7, 12 and 24 being preferred. According to some embodiments, the FABACs of the invention refer to FABACs used to treat, ameliorate, prevent or reduce the risk of dysbiosis and/or associated conditions. Each possibility represents a separate embodiment of the present invention.

A non-limiting general structure of FABACs is set forth below. According to a non-limiting example, a bile acid is conjugated (e.g. using an amide bond, for example at position 3) with 1-2 fatty acids of any of a number of chain lengths. According to exemplary embodiment, the FABAC of the invention is 3β-arachidylamido-7α, 12α, dihydroxy-5β-cholan-24-oic acid (Arachidyl Amido Cholanoic Acid; an amide conjugate of cholic acid with arachidic acid; also known as "Aramchol" or "C20 FABAC") or 3β-stearylamido-7α,12α, dihydroxy-5β-cholan-24-oic acid (Stearyl Amido Cholanoic Acid; an amide conjugate of cholic acid with stearic acid; also known as "Steamchol" or "C18 FABAC"). Each possibility represents a separate embodiment of the present invention.

According to some embodiments, the FABAC of the invention has the Formula I:

$$W\text{—}X\text{-}G \tag{I}$$

wherein G represents a bile acid or a bile salt radical thereof; W represents one or two saturated or unsaturated fatty acid radicals having 6-22 carbon atoms; and wherein X represents a bonding member or a direct C—C or a C═C bond. According to some embodiments, X represents a bonding member selected from the group consisting of: a heteroatom, a direct C—C bond and a C═C bond. Each possibility represents a separate embodiment of the present invention. According to some embodiments, bonding member X is selected from the group consisting of: NH, P, S, O and a direct C═C or C—C bond. Each possibility represents a separate embodiment of the present invention. According to some embodiments, G represents a bile acid radical.

According to some embodiments, the use of FABACs having the Formula II:

$$(W\text{—}X\text{-})_n G \tag{II}$$

wherein G represents a bile acid or a bile salt radical thereof; W represents a fatty acid radical having 6-22 carbon atoms; and wherein X represents a bonding member comprising a heteroatom or a direct C—C or C═C bond; and n is an integer 1 or 2, is contemplated. Each possibility represents a separate embodiment of the present invention. According to some embodiments, the heteroatom is selected from the group consisting of: NH, P, S and O. Each possibility represents a separate embodiment of the present invention. In general, the term "heteroatom" includes atoms of any element other than carbon or hydrogen, preferred examples of which include nitrogen, oxygen, sulfur, and phosphorus.

According to one embodiment n is 1. According to another embodiment n is 2, and at each occurrence W is independently a fatty acid radical having 6-22 carbon atoms and X is independently a bonding member comprising a heteroatom or a direct C—C or C═C bond. Each possibility represents a separate embodiment of the present invention.

In another embodiment, the bonding member of the FABAC is selected from the group consisting of NH, P, S, O, or a direct C—C or C═C bond. Each possibility represents a separate embodiment of the present invention. According to some embodiments, the term "Direct bond" refers, to a C—C(single) bond. In another embodiment, the term "Direct bond" refers to a C═C (double) bond. In another embodiment, more than one direct bond is utilized in the FABAC of the invention. In another embodiment, the bond between the bile acid and the fatty acid radical(s) is in the beta configuration. In another embodiment, the bond between the bile acid and the fatty acid radical(s) is in the alpha configuration. In another embodiment, the bonding member is other than an ester bond.

According to some embodiments, the bile acid or bile acid radical of the FABAC is selected from the group consisting of: cholic acid, ursodeoxycholic acid, chenodeoxycholic acid, deoxycholic acid, lithocholic acid and derivatives thereof. Each type of bile acid or radical thereof represents a separate embodiment of the present invention. The term "radical" as used herein means a chemical moiety comprising one or more unpaired electrons. According to some embodiments, the bile acid or bile acid radical of the FABAC is cholic acid.

According to some embodiments, the FABAC of the invention comprises a single fatty acid radical. The conjugation of the bile acid with the fatty acid radical may take place at various positions of the bile acid. In certain embodiments, the conjugation of the bile acid with the fatty acid radical is performed in a position of the bile acid nucleus selected from the group consisting of: 3, 6, 7, 12 and 24. Each possibility represents a separate embodiment of the present invention. In one embodiment, said conjugation is performed in position 3 of the bile acid nucleus.

According to other embodiments, the FABAC of the invention comprises two fatty acid radicals. According to some embodiments, the conjugation of each fatty acid radical to the bile acid nucleus is at two positions of the bile acid nucleus selected from the group consisting of: 3, 7, 12 and 24. Each possibility represents a separate embodiment of the present invention. According to a particular embodiment, the conjugation of the two fatty acid radicals is at positions 3 and 7 of the bile acid nucleus.

According to some embodiments, the fatty acid is a short-chain fatty acid. According to some embodiments, the chain length of the short-chain fatty acid is 6-8 carbons. According to some embodiments, the fatty acid is a medium-chain fatty acid. According to some embodiments, the chain length of the medium-chain fatty acid is 8-14 carbons. According to some embodiments, the chain length of the fatty acid is 14-22 carbons. According to some embodiments, the chain length of the fatty acid is 16-22 carbons. According to certain embodiments, other fatty acid length known in the art may be utilized. Each type of fatty acid or fatty acid radical represents a separate embodiment of the present invention. According to some embodiments, pharmaceutical compositions according to the disclosed methods comprise more than one type of FABAC.

According to some embodiments, the fatty acid is saturated. According to some embodiments, the fatty acid is unsaturated. According to some embodiments, the fatty acid is mono-unsaturated. According to some embodiments, the fatty acid is poly-unsaturated. Each possibility represents a separate embodiment of the present invention.

According to some embodiments, the one or two fatty acids or fatty acid radicals of the FABACs of the invention are independently selected from the group consisting of: behenic acid, arachidic acid, stearic acid, and palmitic acid. Each possibility represents a separate embodiment of the present invention. An exemplary embodiment of a FABAC according to the present invention is presented in Formula III herein below. According to some embodiments, in Formula III n=20 or n=18. Each possibility represents a separate embodiment of the present invention.

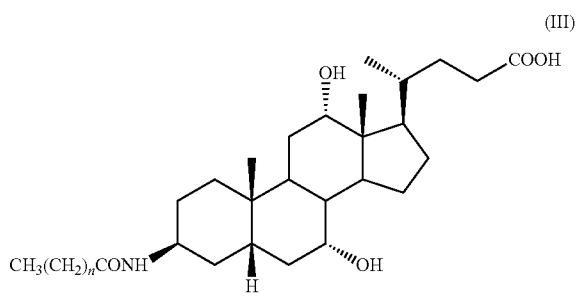

(III)

According to some embodiments, the one or two fatty acids or fatty acid radicals of the FABACs of the invention are unsaturated fatty acids or fatty acid radicals. Each possibility represents a separate embodiment of the present invention. According to some embodiments, the one or two unsaturated fatty acids or unsaturated fatty acid radicals of the FABAC are independently selected from the group consisting of: linolenic acid, eicosapentaenoic acid, docosahexaenoic acid, arachidonic acid, palmitoleic acid, oleic acid and elaidic acid. Each possibility represents a separate embodiment of the present invention.

As used herein, the term "conjugated fatty acid", also known as "CFA", refers to polyunsaturated fatty acids in which at least one pair of double bonds are separated by only one single bond.

In another embodiment, the bonding member is selected from the group consisting of: NH, P, S, O and a direct C—C or C═C bond; each of said one or two fatty acid radicals is a radical of a fatty acid selected from the group consisting of: arachidic acid, stearic acid, behenic acid, palmitic acid, arachidonic acid, eicosapentaenoic acid and oleic acid; and the bile acid is selected from the group consisting of: cholic acid, ursodeoxycholic acid, chenodeoxycholic acid, deoxycholic acid, lithocholic acid and derivatives thereof.

According to some embodiments, the FABAC of methods and compositions of the present invention is selected from the group consisting of: 3β-behenylamido-7α, 12α-dihydroxy-5β-cholan-24-oic acid, 3β-arachidylamido-7α, 12α-dihydroxy-5β-cholan-24-oic acid, 3β-stearylamido-7α, 12α-dihydroxy-5β-cholan-24-oic acid and 3β-palmitylamido-7α, 12α-dihydroxy-5β-cholan-24-oic acid. Each possibility represents a separate embodiment of the present invention. According to exemplary embodiment, the FABAC of the invention is 3β-arachidylamido-7α, 12α, dihydroxy-5β-cholan-24-oic acid (Arachidyl Amido Cholanoic Acid; an amide conjugate of cholic acid with arachidic acid; also known as "Aramchol" or "C20 FABAC"). In another embodiment Aramchol is in the form of Aramchol free acid. In another embodiment Aramchol is in the form of an amine-based salt. In certain particular embodiments, the salt is a meglumine, lysine or tromethamine Aramchol salt. Each possibility represents a separate embodiment of the invention.

FABACs as described herein include pharmaceutically acceptable salts and/or derivatives thereof. Each possibility represents a separate embodiment of the present invention. As used herein, the term "bile acid derivative" includes bile acid salts with their pharmaceutically acceptable bases or acids as well as their diastereoisomeric and enantiomeric forms.

Pharmaceutical Compositions and Kits

Any suitable route may be used to administer the composition of the invention to a subject.

According to some embodiments, suitable administration routes may be systemic routes. According to some embodiments, administering is administering systemically. According to some embodiments, the composition is formulated for systemic administration.

Yet according to other advantageous embodiments, it is hereby disclosed that the FABAC of the invention may be effective even when administered locally (e.g. topically to a GI mucous membrane or by localized administration to a particular segment or region of the GI tract), even when systemic exposure to the active ingredient is reduced or suboptimal. Thus, according to some embodiments, administering is administering locally. According to some embodiments, the composition is formulated for local administration. in other embodiments, the composition is formulated for localized administration, e.g. by infusion by enema or colonoscope or an orogastric, nasogastric, nasoduodenal or nasojejunal tube or any other GI port of entry such as percutaneous endoscopic gastrostomy (PEG) tubes and stomas.

According to other embodiments, a therapeutically effective amount refers to an amount effective to provide a beneficial effect to the subject's microbiota, e.g. when administered locally.

According to another embodiment, administration systemically is through an enteral route. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries or syrups and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin for use in a dispenser may be formulated containing a powder mix of the compound and a suitable powder base, such as lactose or starch.

Solid dosage forms for oral administration include without limitation capsules, tablets, pills, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents. In the case of capsules, tablets and pills, the dosage forms may also comprise buffering agents.

The dosage forms can additionally and advantageously be prepared with a controlled release coating such as enteric coatings. The term "enteric coating", as used herein, refers to a coating which controls the location of composition absorption within the digestive system. Non-limiting examples for materials used for enteric coating are fatty acids, waxes, plant fibers or plastics. In other embodiments, the dosage forms may be prepared with a controlled release matrix, controlling the location of composition absorption within the digestive system. According to various embodiments, the composition is formulated as a controlled release formulation enabling e.g. enhanced or targeted jejunal, duodenal, ileal or colonic delivery of said FABAC. In other words, said formulation may release the active ingredient in a controlled manner so as to provide significantly increased absorption (e.g. by at least 20%, 40%, 60% or 80%) of said active ingredient in the GI region of interest compared to its absorption from conventional immediate release formulations. In other embodiments, said composition is formulated for localized jejunal, duodenal, ileal or colonic delivery by infusion. In another embodiment said composition is formulated for oral or rectal administration. Thus, in certain embodiments, the invention is directed to the use of sustained-release or controlled release formulations of the compounds of Formula (I) as defined herein or salts thereof, including, but not limited to those disclosed by U.S. Pat. No. 6,565,883 For example, the composition may comprise a core coated with two films, the first inner film being a semi-permeable to water or body fluids film applied directly on said core and comprising cellulose acetate, the second outer film being a permeable to water or body fluids film comprising ethylcellulose.

For a formulation of the drug administered at a particular absorption site, the drug level achieved is the outcome of rate constants for (1) release of the drug from the formulation, (2) absorption, and (3) elimination, respectively. For immediate release dosage forms, the rate constant for drug release is far greater than the absorption rate constant. For the controlled release formulations, the opposite is true, such that the rate of release of drug from the dosage form is the rate-limiting step in the delivery of the drug to the target area. The term "controlled release" as used herein is intended to include any non-immediate release formulation, including but not limited to sustained release, delayed release and pulsatile release formulations.

A controlled release formulation may comprise, for example, controlled release beads comprising the drug. A common type of controlled release beads comprises an inert core, such as a sugar sphere, coated with an inner drug-containing layer and an outer membrane layer controlling drug release from the inner layer. An example of such controlled release beads is described in U.S. Pat. No. 5,783,215 where each bead comprises (i) a core unit of a soluble or insoluble inert material, (ii) a first layer on the core unit comprising an active ingredient dispersed in a hydrophilic polymer, (iii) an optional second layer of hydrophilic polymer covering the first layer, and (iv) an outermost membrane layer effective for controlled release of the active ingredient. In the above and similar controlled release beads it is not uncommon to apply a "sealcoat" in the form of a small amount (e.g. 1-3%) of a water-soluble polymer, such as hydroxypropylmethyl cellulose (HPMC) or polyvinylpyrrolidone (PVP), between the inert core and the layer containing the active ingredient. The purpose thereof is generally to isolate the drug from the core surface in the event that a drug-core chemical interaction is possible, and/or to smooth the surface of the inert core such that the surface area is more consistent from lot to lot to thereby improve the coating quality when the drug layer and the controlled release membrane layers are applied.

The cores are typically of a water-soluble or swellable material, and may be any such material that is conventionally used as cores or any other pharmaceutically acceptable water-soluble or water-swellable material made into beads or pellets. Especially, the beads are spheres of sucrose/starch (Sugar Spheres NF), sucrose crystals, or extruded and dried spheres typically comprised of excipients such as microcrystalline cellulose and lactose.

The substantially water-insoluble material in the first or sealcoat layer is generally a "GI insoluble" or "GI partially insoluble" film forming polymer (latex or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates, or any other pharmaceutically acceptable polymer.

In a particular embodiment, the composition is a controlled release formulation formulated for colonic delivery. For example, colonic delivery systems are disclosed in U.S. Pat. Nos. 5,525,634 and 5,866,619 to some of the inventors of the present invention.

Liquid dosage forms for oral administration may further contain adjuvants, such as wetting agents, emulsifying and suspending agents, and sweetening, flavoring and perfuming agents.

The pharmaceutical composition of the present invention may also be formulated in rectal compositions such as suppositories or retention enemas, using, for example, conventional suppository bases such as cocoa butter or other glycerides. According to some embodiments, the present disclosure relates to a pharmaceutical composition comprising a therapeutically effective amount of a fatty acid bile acid conjugate (FABAC) of Formula I as defined herein. According to some embodiments, the present disclosure relates to a pharmaceutical composition comprising a therapeutically effective amount of a 3β-arachidylamido-7α, 12α-dihydroxy-5β-cholan-24-oic acid. According to other embodiments, the pharmaceutical composition comprises the FABAC of the invention (or in other embodiments a combination of FABACs of the invention) as sole active ingredient. In a particular embodiment the composition comprises Aramchol as the sole active ingredient. For example, without limitation, an effective amount for oral administration to human subjects may be a daily dose of 10-800 mg, 30-700 mg, 50-600 mg, 10-400 mg or 300-600 mg.

The pharmaceutical compositions and kits of the invention may optionally further comprise additional active ingredients, including, but not limited to, antimicrobial (e.g. antibiotic), probiotic and prebiotic agents. In another embodiment, the invention relates to pharmaceutical compositions and kits comprising a therapeutically effective amount of a FABAC of Formula I (e.g. Aramchol or a pharmaceutically acceptable salt thereof), in combination with at least one antibiotic, probiotic or prebiotic agent. In another embodiment said composition comprises a plurality of antibiotic, probiotic and/or prebiotic agents.

As used herein, the term "antimicrobial" refers to a compound or element that inhibits the growth or kills microorganisms. Antimicrobial agents include, but are not limited to, compounds such as antibiotics produced naturally or synthetically. As used herein, the term "antibiotic" denotes an antimicrobial agent that inhibits bacterial growth or kills bacteria. The term "antibacterial" is often used synonymously with the term antibiotic(s). The term "antimicrobial" denotes a broader range of compounds providing efficacy against the causative agents of one or more infectious diseases, including e.g. antibacterial, anti-fungal and anti-parasitic agents.

Antimicrobial agents may be produced by known synthetic methods or isolated from their natural source, and various antimicrobial drugs are available commercially. Exemplary antibiotic agents include, without limitation, nitroimidazoles, macrolides and beta-lactams. Various nitroimidazole drugs capable of inhibiting nucleic acid synthesis and/or disrupting microbial DNA were developed against anaerobic bacterial and parasitic infections, and include 2, 4- and 5-nitroimidazoles (classified according to the location of the nitro functional group). Drugs of the 5-nitro variety include e.g. metronidazole (Flagyl), tinidazole, nimorazole, dimetridazole, 6-Amino PA824, ornidazole, megazol, and azanidazole. Drugs based on 2-nitroimidazoles include e.g. benznidazole. The macrolides are a class of natural products having a large macrocyclic lactone ring to which one or more deoxy sugars, usually cladinose and desosamine, may be attached. Various macrolides having protein synthesis inhibitory activity were developed as antibiotic agents (e.g. Azithromycin, Clarithromycin, Erythromycin, Fidaxomicin, and Telithromycin). Polyene antimycotics such as amphotericin B and nystatin manifests antifugal activity. β-lactam antibiotics (or beta-lactams) are a class of broad-spectrum antibiotics, consisting of all antibiotic agents that contain a β-lactam ring in their molecular structures. This includes penicillin derivatives (penams), cephalosporins (cephems), monobactams, and carbapenems. Their activity includes inhibiting the synthesis of the peptidoglycan layer of bacterial cell walls.

As used herein, the term "probiotic" refers to a live microbial agent that is beneficial to health. Typically, this term denotes compositions comprising ingestible live microbial cultures such as bacterial cultures, which survive transit through the gastrointestinal tract and beneficially affect the host by improving its intestinal microbial balance. Exemplary probiotic agents include, but are not limited to, *lactobacillus* species such as *Lactobacillus casei, Lactobacillus plantarum, Lactobacillus acidophilus*, and *Lactobacillus rhamnosus*, as well as other lactic acid-producing bacteria such as *Bifidobacterium* species. Probiotic agents may be formulated for oral administration e.g. in the form of tablets, pills, capsules, lozenges, granules, powders, suspensions, sachets, pastilles, sweets, bars, syrups and corresponding administration forms, which may be in the form of a unit dose. The probiotic composition may typically comprise $10^5$ to $10^{13}$ colony forming units (cfu), preferably at least $10^6$ cfu, $10^7$ cfu, $10^8$ cfu, or $10^9$ cfu per gr dry weight of the composition. Probiotic agents may also be delivered via other enteral routes, such as by enema, colonoscopy, asogastric or nasoduodenal tube. For example, the probiotic agent may be a fecal microbiota transplant (FMT), namely a preparation of fecal matter containing bacteria (and typically further containing natural antibacterials), introduced directly into the GI tract of the recipient. FMT are typically produced by collecting a stool sample from a tested healthy donor, mixing the sample with a saline or other solution, straining the resulting solution, and placing the resulting FMT in the patient e.g. by enema, orogastric tube or by mouth in the form of a capsule containing freeze-dried material.

As used herein, the term "prebiotic" refers to a digestion-resistant food ingredient that beneficially affects a human and/or other animal that ingests the prebiotic. In preferred embodiments, prebiotics selectively stimulate the growth and/or activity of a limited number of bacterial types in the intestinal tract, such that the health of the human and/or other animal is improved. Examples for prebiotics are resistant starch, fructo-oligosaccharides, galacto-oligosaccharides, xylo-oligosaccharides, polydextrose, lactulose, inulin or soluble fiber (e.g. *psyllium* husk or acacia fibers). Other exemplary prebiotic agents are lignin, cellulose, hemicelluloses, β-glucans, pectin, gums and dextrin.

In another embodiment of the invention, said composition or kit may comprise ursodeoxycholic acid or other substances aimed at modification of the entero-hepatic cycle and cholesterol metabolism. In yet another embodiment said composition or kit does not comprise (or said FABAC is not administered with) ursodeoxycholic acid. In another embodiment said composition or kit does not comprise (or said FABAC is not administered with) a branched glycan comprising glucose, galactose, arabinose, mannose, fructose, xylose, fucose, or rhamnose glycan units. Each possibility represents a separate embodiment of the invention.

Therapeutic Use

According to certain embodiments, the compositions, methods, kits and medicaments of the invention are used for treating or preventing dysbiosis in a subject in need thereof. In other embodiments, the compositions, methods, kits and medicaments of the invention are used for promoting the growth of beneficial microbiota in the GI tract. In other embodiments, the compositions, methods, kits and medicaments of the invention are used for inhibiting the growth of detrimental microbiota in the GI tract. In other embodiments, the compositions, methods, kits and medicaments of the invention are used for modifying (e.g. enhancing) microbiota biodiversity in the GI tract. Each possibility represents a separate embodiment of the invention. In other embodiments, the compositions, methods, kits and medicaments of the invention are used for treating or preventing the appearance of symptoms of dysbiosis in a subject in need thereof. In some embodiments, symptoms of dysbiosis may include but are not limited to, abdominal distension, regular/frequent episodes of diarrhea, frequent stools, recent onset/chronic diarrhea or diarrhea for 1-3 months, poor tolerance/intolerance of sugars, flatulence, rotten egg burps, meal-related bloating, and constant fatigue. Each possibility represents a separate embodiment of the invention.

As used herein, the terms "gastrointestinal" and "GI" refer to the stomach and intestines in the digestive tract of humans and other animals. However, as also used in context herein, the term "gastrointestinal tract" ("GI tract") refers to the entire alimentary canal, from the oral cavity to the rectum. The term encompasses the tube that extends from the mouth to the anus, in which the movement of muscles and release of hormones and enzymes digest food. The gastrointestinal tract starts with the mouth and proceeds to the esophagus, stomach, small intestine, large intestine, rectum and, finally, the anus. As used herein, the terms "gastrointestinal" and "GI tract" are not intended to include accessory organs of digestion, such as the liver, gallbladder, and pancreas.

As used herein, gastrointestinal diseases and disorders, further referred to collectively as gastrointestinal pathologies, denote diseases and disorders that primarily affect the GI tract. GI pathologies to be treated, prevented or alleviated by the compositions, methods and kits of the invention are associated with dysbiosis or alteration of intestinal floral balance (as part of their etiology and/or pathology). Such dysbiosis or alteration may in various embodiments result from, or be associated with, chronic inflammatory reactions, autoimmune reactions, infections (e.g. bacterial, viral or parasitic), bowel resection, and/or chronic diarrhea.

In other embodiments, the compositions, methods, kits and medicaments of the invention are used for preventing and/or treating a gastrointestinal pathology associated with alternation of intestinal flora balance in a subject in need thereof. In other embodiments, the compositions, methods, kits and medicaments of the invention are used for treating and/or preventing a gastrointestinal pathology associated with a chronic inflammatory disease, an autoimmune disease, an infection, bowel resection, and/or a condition associated with chronic diarrhea. In other embodiments, the compositions, methods, kits and medicaments of the invention are used for treating and/or preventing irritable bowel syndrome (IBS), inflammatory bowel disease (IBD), short bowel syndrome (SBS), celiac disease, small intestinal bacterial overgrowth (SIBO), gastroenteritis, leaky gut syndrome, and gastrointestinal lymphoma, or a pathology associated with a bacterial, viral or parasitic infection or overgrowth. In other embodiments, the compositions, methods, kits and medicaments of the invention are used in combination with at least one antibiotic, probiotic or prebiotic agent, for the treatment or prevention of dysbiosis or a gastrointestinal pathology associated therewith. Each possibility represents a separate embodiment of the invention.

Chronic inflammatory GI diseases include, without limitation, IBS and IBD. Autoimmune GI diseases include, without limitation, Celiac disease. GI pathologies associated with an infection include, without limitation pathologies associated with a bacterial, viral or parasitic infection or overgrowth. In an embodiment, the infection or overgrowth is of a pathogenic bacterium including, but not limited to *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella*, or *Bacillus* spp. In another embodiment, said infection is of drug-resistant bacteria such as antibiotic-resistant bacteria, including, but not limited to multi-drug resistant bacteria, Carbapenem-resistant Enterobacteriaceae (CRE), extended spectrum beta-lactam resistant Enterococci (ESBL), and vancomycin-resistant Enterococci (VRE).

Chronic diarrhea, defined as a decrease in stool consistency for more than four weeks, may be caused by various pathologies (including, but not limited to IBD and IBS), infection or digestive problems.

Crohn's disease is characterized by ulcerations of the small and/or large intestines, but can affect the digestive system anywhere from the mouth to the anus. Various terms are used to describe Crohn's disease, and tend to reflect the portion of the gastrointestinal tract affected. For example, involvement of the large intestine (colon) only has been termed Crohn's colitis or granulomatous colitis, while involvement of the small intestine only has been termed Crohn's enteritis. Disease in the terminal portion of the small intestine i.e. the ileum, has been termed Crohn's ileitis. When both the small intestine and the large intestine are involved, the condition has been termed Crohn's enterocolitis or ileocolitis. Ulcerative colitis is a condition related to Crohn's disease that involves only the colon, and collectively these diseases are frequently referred to as inflammatory bowel disease (IBD).

Irritable bowel syndrome (IBS) is a common disorder that has a pronounced effect on the quality of life and that accounts for a large proportion of healthcare costs. The disorder is characterized by lower abdominal pain, bloating, diarrhea, constipation, or constipation alternating with diarrhea. Altered bowel motility, visceral hyperalgesia, food allergy, bacterial overgrowth, psychosomatic factors, stress associated with the myenteric nervous system have all been proposed as playing a part in the pathogenesis of IBS. Gastrointestinal inflammation may also be associated with irritable bowel syndrome, along with stress.

Short bowel syndrome (SBS) is a malabsorption disorder caused by a lack of functional small intestine. SBS occurs in subjects having less than 2 m of working bowel, resulting in intestinal failure (decreased intestinal function such that nutrients, water, and electrolytes are not sufficiently absorbed). The primary symptom is diarrhea, which can result in dehydration, malnutrition, and weight loss. Other symptoms may include bloating, heartburn, feeling tired, lactose intolerance, and foul smelling stool.

Celiac disease is an autoimmune disease manifested in genetically susceptible people caused by intolerance to gluten, resulting in mucosal inflammation and villous atrophy, which causes malabsorption. Symptoms usually include diarrhea and abdominal discomfort. Diagnosis is by small-bowel biopsies showing characteristic though not specific pathologic changes of villous atrophy that resolve with a strict gluten-free diet.

Small intestinal bacterial overgrowth (SIBO), also termed small bowel bacterial overgrowth syndrome, is a disorder of excessive bacterial growth in the small intestine (bacterial counts of $>10^5$/mL). SIBO can result from alterations in intestinal anatomy (e.g. due to surgery or partial obstruction) or GI motility, or from lack of gastric acid secretion. This condition can lead to vitamin deficiencies, fat malabsorption, and undernutrition. The most frequent symptoms are abdominal discomfort, diarrhea, bloating, and excess flatulence.

Gastroenteritis, is inflammation of the lining of the stomach and small and large intestines. Most cases are infectious, although gastroenteritis may occur after ingestion of drugs and chemical toxins (e.g., metals or plant substances). Symptoms include anorexia, nausea, vomiting, diarrhea, and abdominal discomfort. Treatment is symptomatic, with certain parasitic and bacterial infections requiring specific anti-microbial therapy.

Increased intestinal permeability (abnormally excessive opening of intercellular tight junctions) allows passage of microbes, microbial products, and foreign antigens into the mucosa and bloodstream, with subsequent possible development of immune and/or inflammatory reactions. Such reactions, collectively referred to as "leaky gut syndrome", may result in chronic inflammation and be associated with the development of additional GI pathologies such as celiac disease, Crohn's disease and IBS. Gastrointestinal lymphomas include, but are not limited to, primary GI tract lymphomas (typically of the non-Hodgkin type) such as mucosa-associated lymphoid tissue (MALT) lymphoma in stomach, mantle cell lymphoma in terminal ileum, jejunum and colon, as well as enteropathy-associated T-cell lymphoma in jejunum, and follicular lymphoma in duodenum.

In other embodiments, the compositions, methods, kits and medicaments of the invention comprise, or are used in combination with, at least one antibiotic, probiotic or prebiotic agent. Exemplary antibiotic agents include, but are not limited to, nitroimidazole, macrolide, and beta-lactam antibiotics. Exemplary prebiotic agents include, but are not limited to, lactulose, lignin, cellulose, hemicelluloses, β-glucans, pectin, gums, resistant starch, dextrin, *psyllium*, inulin, fructooligosaccharides, and polydextrose. Exemplary probiotic agents include, but are not limited to, various *lactobacillus* species or a fecal microbiota transplant (FMT). In other embodiments, the compositions, methods, kits and medicaments of the invention are used in combination with a specialized diet, including, but not limited to, enteral or parentearal liquid formulations, reported to be associated with the development of dysbiosis, or a diet prescribed for the management of dysbiosis. According to exemplary embodiments, the compositions, methods, kits and medicaments of the invention are used in combination with fiber-enriched, fructose-reduced, elemental, total liquid enteral, total parenteral, and peripheral parenteral diet. Liquid enteral diet refers to the introduction of a nutritionally complete liquid formula directly into the stomach or small intestine via a designated (e.g. nasogastric) tube. Parenteral diet (parenteral nutrition) refers to the delivery of liquid nutrition into a vein. When the diet is used as the exclusive source of nutrition, it is referred to as total liquid enteral diet, or total parenteral diet, respectively. Elemental diet comprises liquid nutrients in an easily assimilated form (for example, nitrogen is provided in the form of free amino acids rather than as whole or partial protein). It is usually composed of amino acids, fats, sugars, vitamins, and minerals. Elemental diet may be administered orally or by use of a gastric feeding tube or intravenous feeding. Fiber enriched diet typically refers to specialized fiber-enriched enteral formulations (e.g. Nutrison multifibre, containing 1.5 g/100 ml of soluble and non-soluble fibers at a 1:1 ratio), but may also refer in some embodiments to prescribed oral diets including daily ingestion of e.g. 30 gr of fiber or more. Fructose-reduced diets may be e.g. low-fermentable oligosaccharides, disaccharides, monosaccharides, and polyol (FODMAP) diet, or enteral nutrition formulations devoid of added fructose.

According particular embodiments, the compositions of the invention are administered locally to a particular site of the GI tract, e.g. in combination with a FMT. Each possibility represents a separate embodiment of the invention.

The subject to be treated by the compositions, methods pharmaceutical packs and medicaments of the invention, also referred to herein as a subject in need thereof, is a mammalian and preferably a human subject. In certain embodiments, the subject has been diagnosed as suffering from dysbiosis. In certain other embodiments, the subject is at risk for developing dysbiosis. Each possibility represents a separate embodiment of the invention.

Various methods for diagnosing dysbiosis are known in the art, and include without limitation, breath-testing methods, small-bowel culture techniques and culture-independent techniques such as high-throughput next-generation sequencing. For example, the Comprehensive Digestive Stool Analysis (CDSA, a non-invasive evaluation of gastrointestinal function that includes analyses of digestion, absorption, bacterial balance, yeast and parasites), or the GA-map Dysbiosis Test (Genetic Analysis AS, Oslo, Norway, based on DNA profiling using probes targeting variable regions of the bacterial 16S rRNA gene), may be used.

In various embodiments, a subject at risk of developing dysbiosis is under a treatment regimen with at least one agent selected from the group consisting of anti microbial agents, parenteral nutrition, or immune suppressive agents, wherein each possibility represents a separate embodiment of the invention Immune suppressive agents are drugs that inhibit or prevent activity of the immune system, including, but not limited to glucocorticoids, cytostatics, antibodies and drugs acting on immunophilins.

Known indications suggested for FABAC treatment include those disclosed in U.S. Pat. Nos. 6,384,024, 6,395, 722, 6,589,946, 7,501,403, 8,110,564 and 8,975,246, as detailed herein. In contradistinction, the present specification surprisingly discloses that FABAC may provide therapeutic and/or prophylactic benefits in the management of dysbiosis. It is herein disclosed for the first time that therapeutic regimens comprising FABACs or Aramchol in particular are particularly advantageous in patients suffering from dysbiosis, or a condition associated therewith. Accordingly, the methods of the invention advantageously comprise the step of identifying the subject as being afflicted with dysbiosis (or the associated condition), prior to administration of the FABACs of the invention. In certain embodiments, the subject is not concomitantly afflicted with an additional condition (such as diabetes, non-alcoholic fatty liver disease, non-alcoholic seatohepatitis, or other known indications for FABAC treatment as detailed above). In a particular embodiment said subject is not afflicted with a liver disease. Each possibility represents a separate embodiment of the invention.

The following examples are presented in order to more fully illustrate some embodiments of the invention. They should, in no way be construed, however, as limiting the broad scope of the invention.

EXAMPLES

Example 1. Localized Treatment of Inflammatory Bowel Disease by Aramchol

Colitis is induced in male rats weighing 250 g by intracolonic administration under light ether inhalation anesthesia of 1 ml of dinitrobenzensulfonic acid (DNBS) (20 mg/ml, in ethanol 30% v/v). The solution is instilled slowly over 20 seconds via a flexible, perforated Foley catheter, which was then immediately removed. The rats are placed in an upside down position for another 40 seconds. The control group is treated with saline instead of Aramchol using the same procedure.

Treatment Groups:

Group 1 is given Aramchol (30 mg/kg, 50 mg/kg or 80 mg/kg) intra-rectally one hour prior to induction of colitis, and then 12, 24, 36, 48 and 60 hours later.

Group 2 is given saline instead of Aramchol.

Group 3 is given saline instead of DNBS.

Group 4 is given 200 μg of the steroid drug budesonide (in 1 ml of hydroalcoholic solution), intra-rectally one hour after the induction of colitis, and then 12, 24, 36, 48 and 60 hours later (altogether: 1.2 mg budesonide).

Group 5 is given 1 ml saline instead of budesonide.

Group 6 is given saline instead of DNBS.

The rats are anesthetized by ketamine (100 mg/kg body weight) given by intraperitoneal injection and the colon is exposed through a longitudinal abdominal incision. The distal 10 cm of the colon is removed, cut open and rinsed with ice-cold saline. Euthanasia of the anesthetized rats is performed by puncturing of the chest wall.

The fresh tissues are scored for presence of (1) edema, (2) hyperemia and (3) number and areas of mucosal ulcers. If present, the total area of all ulcers is taken. They are then blotted dry, weighed and immediately frozen in liquid nitrogen. On the day of analysis the colon specimens are warmed to 4° C., homogenized (Polytron, Kinematica GmbH, Germany) in 10 volumes of 0.02M phosphate-buffer, pH 7.4, and stored at −74° C. for biochemical analysis of inflammatory markers.

In additional experiments, Aramchol (30 mg/kg, 50 mg/kg or 80 mg/kg) or vehicle is given by oral gavage, and colitis is induced and evaluated as described above.

In additional experiments in a model of Crohn's ileits, DNBS and Aramchol (30 mg/kg, 50 mg/kg or 80 mg/kg) or vehicle are targeted to specific components of the small intestine by administration via nasogastric or nasojejunal tubing. The targeted intestinal segments are then collected and evaluated as described above.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating dysbiosis of the gastrointestinal (GI) tract or a gastrointestinal pathology associated with pathogenic alteration of an intestinal flora balance in a subject in need thereof, the comprising administering a composition comprising a therapeutically effective amount of 3β-arachidylamido-7α, 12α-dihydroxy-5-cholan-24-oic acid (Aramchol), or a pharmaceutically acceptable salt thereof.

2. The method of claim 1 for promoting the growth of beneficial microbiota in the GI tract.

3. The method of claim 1 for inhibiting the growth of detrimental microbiota in the GI tract.

4. The method of claim 1 for modifying microbiota biodiversity in the GI tract.

5. The method of claim 1, wherein the dysbiosis is associated with a gastrointestinal disease or disorder.

6. The method of claim 5, wherein said dysbiosis is associated with a chronic inflammatory disease, an autoimmune disease, an infection, bowel resection, and/or a condition associated with chronic diarrhea.

7. The method of claim 6, wherein the disease or disorder is selected from the group consisting of: irritable bowel syndrome (IBS), inflammatory bowel disease (IBD), short bowel syndrome (SBS), celiac disease, small intestinal bacterial overgrowth (SIBO), gastroenteritis, leaky gut syndrome, and gastric lymphoma.

8. The method of claim 6, wherein the disease or disorder is associated with a bacterial, viral or parasitic infection or overgrowth.

9. The method of claim 8, wherein the disease or disorder is associated with infection by drug-resistant bacteria.

10. The method of claim 1, wherein the subject is human.

11. The method of claim 10, wherein said subject is under a treatment regimen with at least one of anti microbial agents, parenteral nutrition, or immune suppressive agents.

12. The method of claim 1, wherein said composition comprises the aramchol as a sole active ingredient.

13. The method of claim 1, wherein said composition further comprises at least one antibiotic, probiotic or prebiotic agent.

14. The method of claim 1, wherein said composition is used in combination with a fecal microbiota transplant (FMT).

15. The method of claim 1, wherein said composition is formulated for oral or rectal administration.

16. The method of claim 1, wherein said composition is formulated as a controlled release formulation enabling jejunal, duodenal, ileal or colonic delivery of said aramchol.

17. The method of claim 1, wherein said composition is for localized jejunal, duodenal, ileal or colonic delivery by infusion.

18. The method of claim 1, wherein said composition is formulated for rectal administration.

19. The method of claim 1, wherein said composition is for use in combination with a diet selected from the group consisting of: fiber-enriched, fructose-reduced, elemental, total liquid enteral, total parenteral, and peripheral parenteral diet.

20. The method of claim 13, wherein the antibiotic agent is selected from the group consisting of nitroimidazoles, macrolides, and beta-lactams.

21. The method of claim 13, wherein the probiotic agent comprises at least one of *Lactobacillus casei, Lactobacillus plantarum, Lactobacillus acidophilus*, and *Lactobacillus rhamnosus*.

22. The method of claim 13, wherein the probiotic agent is a fecal microbiota transplant (FMT).

23. The method of claim 13, wherein the prebiotic agent is selected from the group consisting of lactulose, lignin, cellulose, hemicelluloses, β-glucans, pectin, gums, resistant starch, dextrin, *psyllium*, inulin, fructooligosaccharides, and polydextrose.

* * * * *